United States Patent
Sun et al.

(10) Patent No.: US 10,966,909 B2
(45) Date of Patent: *Apr. 6, 2021

(54) RESIN COMPOSITES FOR USE IN DENTAL PREVENTIVE AND RESTORATIVE APPLICATIONS

(71) Applicant: ADA Foundation, Chicago, IL (US)

(72) Inventors: Jirun Sun, Rockville, MD (US); Rafael Lee Bowen, Gaithersburg, MD (US)

(73) Assignee: ADA Foundation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/895,488

(22) Filed: Jun. 8, 2020

(65) Prior Publication Data
US 2020/0297587 A1    Sep. 24, 2020

Related U.S. Application Data

(60) Continuation of application No. 16/356,959, filed on Mar. 18, 2019, now Pat. No. 10,675,224, which is a division of application No. 15/345,733, filed on Nov. 8, 2016, now Pat. No. 10,231,906, which is a continuation of application No. 14/660,466, filed on Mar. 17, 2015, now Pat. No. 9,572,753.

(60) Provisional application No. 61/953,956, filed on Mar. 17, 2014.

(51) Int. Cl.
*A61K 6/887*   (2020.01)
*A61K 6/889*   (2020.01)

(52) U.S. Cl.
CPC .............. *A61K 6/887* (2020.01); *A61K 6/889* (2020.01)

(58) Field of Classification Search
None
See application file for complete search history.

(56) References Cited

U.S. PATENT DOCUMENTS

| | | | | |
|---|---|---|---|---|
| 6,124,070 A * | 9/2000 | Baba | ............... | G03G 9/0819 |
| | | | | 430/109.3 |
| 7,241,856 B2 * | 7/2007 | Jin | .................. | A61K 6/887 |
| | | | | 528/301 |
| 8,263,725 B2 * | 9/2012 | Ichiryu | ........... | C08G 59/306 |
| | | | | 528/27 |
| 9,572,753 B2 * | 2/2017 | Sun | ................. | A61K 6/887 |

(Continued)

*Primary Examiner* — Peter A Salamon

(57) ABSTRACT

A composition of matter includes one or more functionalized vinylbenzyl components of the formula

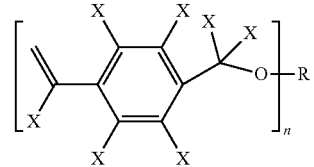

covalently connected to one or more R functional components; the one or more R functional groups selected from a group including one or more hydroxyl methyl (—CHOH—) moieties and/or derivatives thereof, one or more ethoxy (—CH$_2$—CH$_2$—O—) moieties and/or derivatives thereof, end one or more benzene (C$_6$H$_6$) and/or derivatives thereof; and ether links that connect the functionalized vinylbenzyl components and the R functional components.

3 Claims, 12 Drawing Sheets

(56) References Cited

U.S. PATENT DOCUMENTS

| | | | |
|---|---|---|---|
| 2007/0105040 A1* | 5/2007 | Toukhy | G03F 7/0392 |
| | | | 430/270.1 |
| 2009/0104559 A1* | 4/2009 | Houlihan | G03F 7/0392 |
| | | | 430/270.1 |
| 2009/0104561 A1* | 4/2009 | Hawker | G03H 1/02 |
| | | | 430/270.15 |
| 2009/0188622 A1* | 7/2009 | Bowen | C09J 101/30 |
| | | | 156/305 |
| 2010/0119972 A1* | 5/2010 | Houlihan | G03F 7/095 |
| | | | 430/281.1 |
| 2010/0150511 A1* | 6/2010 | Arsenault | C08J 5/18 |
| | | | 385/130 |
| 2010/0222525 A1* | 9/2010 | Ichiryu | C08G 59/3254 |
| | | | 525/476 |
| 2012/0044970 A1* | 2/2012 | Arsenault | G01K 11/125 |
| | | | 374/159 |
| 2012/0308939 A1* | 12/2012 | Kudo | G03F 7/091 |
| | | | 430/326 |

* cited by examiner

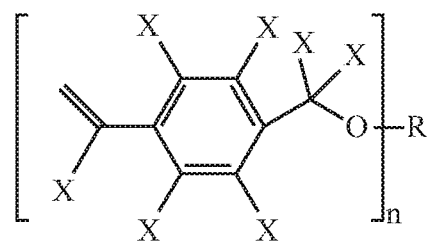
FIG. 3A
FIG. 3B
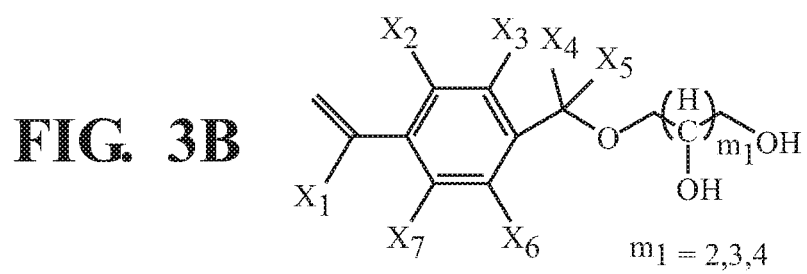
FIG. 3C
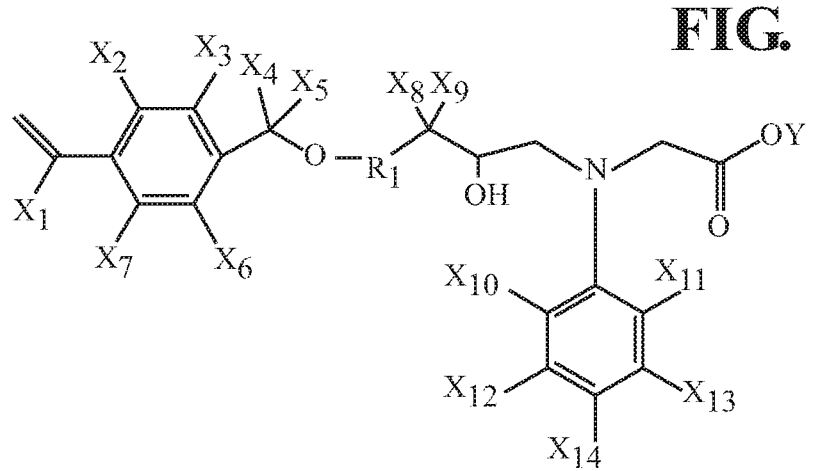

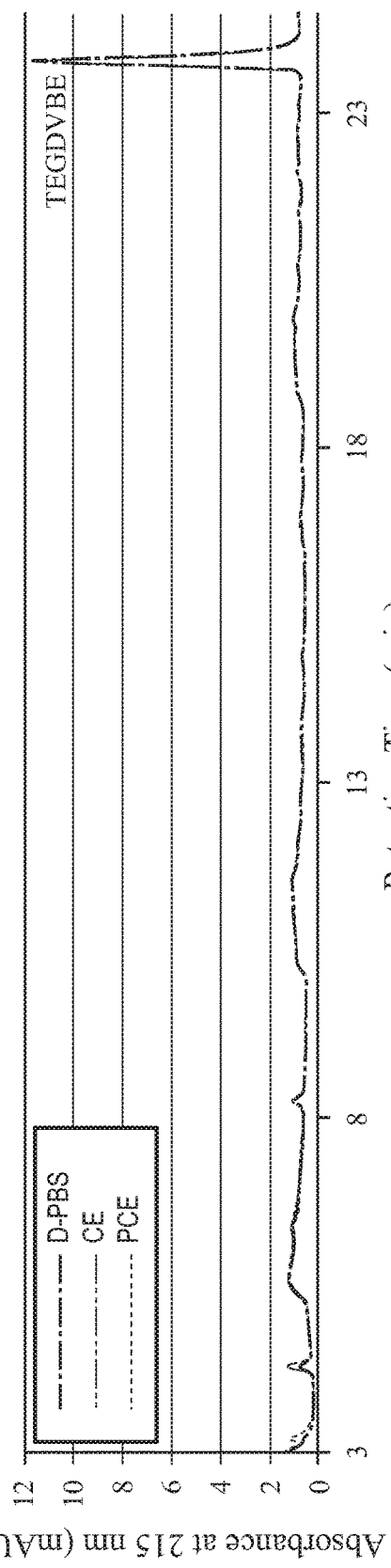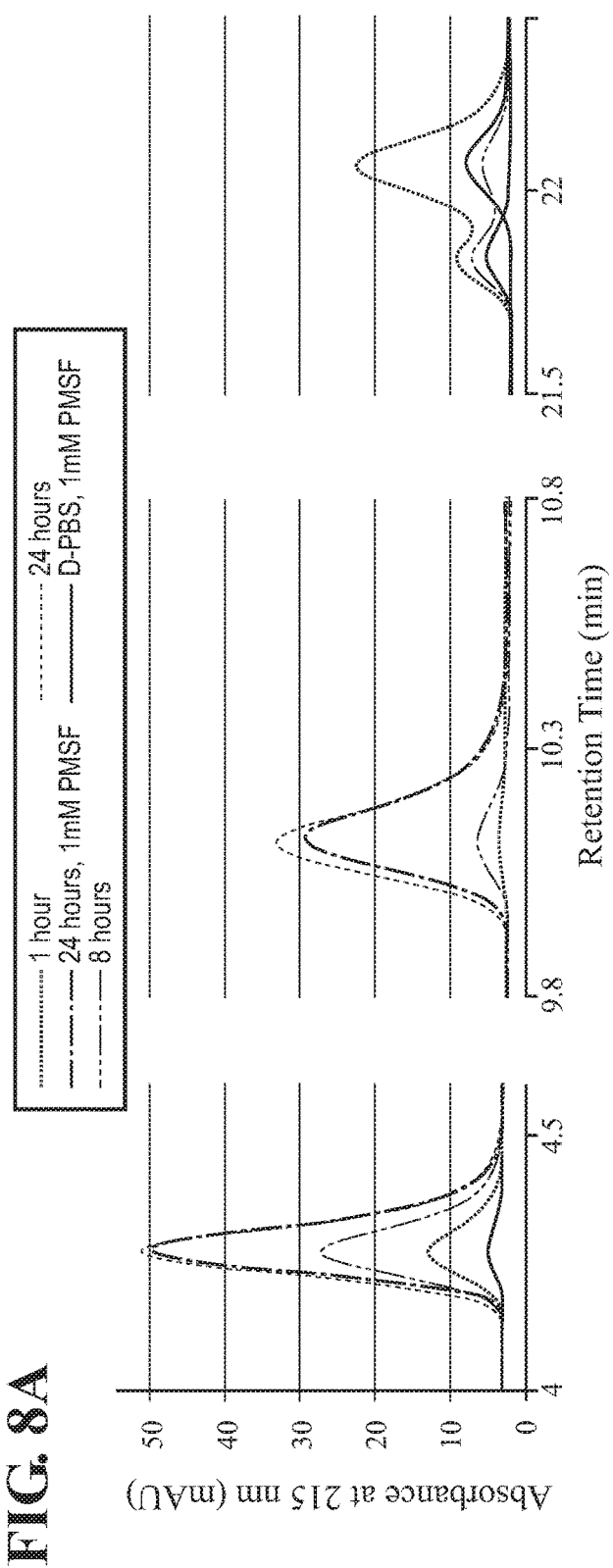

RESIN COMPOSITES FOR USE IN DENTAL PREVENTIVE AND RESTORATIVE APPLICATIONS

RELATED APPLICATIONS

This application is a continuation U.S. patent application Ser. No. 16/356,959, filed Mar. 18, 2019, entitled "ENZYMATICALLY AND HYDROLYTICALLY STABLE DENTAL PREVENTIVE AND RESTORATIVE SYSTEMS," which is a division of U.S. patent application Ser. No. 15/345,733, now U.S. Pat. No. 10,231,906, filed Nov. 8, 2016 and entitled "ENZYMATICALLY AND HYDROLYTICALLY STABLE DENTAL PREVENTIVE AND RESTORATIVE SYSTEMS," which is a continuation of U.S. patent application Ser. No. 14/660,466 filed Mar. 17, 2015, now U.S. Pat. No. 9,572,753, filed Mar. 17, 2015, entitled "ENZYMATICALLY AND HYDROLYTICALLY STABLE RESINS, RESIN MONOMERS, AND RESIN COMPOSITES FOR USE IN DENTAL PREVENTIVE AND RESTORATIVE APPLICATIONS," which claims the benefit of U.S. Provisional Application Ser. No. 61/953,956 filed Mar. 17, 2014, and entitled "ENZYMATICALLY AND HYDROLYTICALLY STABLE RESINS RESIN MONOMERS, AND RESIN COMPOSITES FOR USE IN DENTAL PREVENTIVE AND RESTORATIVE APPLICATIONS,". The disclosures of these applications are incorporated by reference.

STATEMENT OF FEDERALLY SPONSORED RESEARCH

The invention was made with government support under grant U01 DE023752 awarded by the National Institutes of Health. The U.S. government has certain rights in the invention.

BACKGROUND

Some current dental restorative applications may include: 1) a bisphenol A glycidyl methacrylate/triethylene glycol dimethacrylate (Bis-GMA/TEG-DMA) (see FIG. 1), and/or a urethane dimethacrylate-based polymer to provide a resin network, 2) reinforcing filler particles treated with coupling agents (containing hydrolyzable ester connecting groups) to bind the resin to the particles, and 3) bonding agents (also containing hydrolyzable ester connecting groups). These systems and their accompanying use instructions may not produce satisfactory durability and esthetics over time. In addition to a short average service life, these systems are subject to leaching of unreacted monomers, bisphenol A (BPA), and system degradation products.

SUMMARY

Disclosed are enzymatically and hydrolytically stable resins for dental applications, and methods for producing such resin monomers that can yield highly cross-linked, strong and durable polymers. The resins and resin monomers for use in restorative dentistry withstand the challenging conditions of the oral environment; however, the resins and resin monomers may be useful in additional strategic applications.

In an embodiment, A composition of matter includes one or more functionalized vinylbenzyl components of the formula

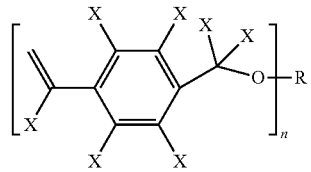

covalently connected to one or more R functional components; the one or more R functional groups selected from a group including one or more hydroxyl methyl (—CHOH—) moieties and/or derivatives thereof, one or more ethoxy (—$CH_2$—$CH_2$—O—) moieties and/or derivatives thereof, and one or more benzene ($C_6H_6$) and/or derivatives thereof; and ether links that connect the functionalized vinylbenzyl components and the R functional components.

Also disclosed in a composition of matter consisting of one monomer or a mixture of monomers that include one or more functionalized vinylbenzyl components of the formula

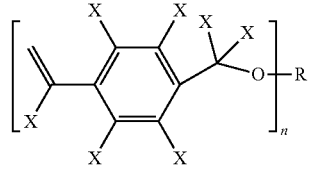

covalently connected to one or more R functional components. The one or more R functional groups are selected from a group including one or more hydroxyl methyl (—CHOH—) moieties and/or derivatives thereof, one or more ethoxy (—$CH_2$—$CH_2$—O—) moieties and/or derivatives thereof, and one or more benzene (C6H6) and/or derivatives thereof; and ether links that connect the functionalized vinylbenzyl components and the R functional components, or the functionalized vinylbenzyloxy(s) and the R components(s) are linked through one or more moieties chosen from a group consisting of alkyl (—$CH_2$—, —$CH_2CH_2$—, —$C_3H_6$—, —C(i-propyl)$_2$-, and —$C_4H_8$—); alkoxy (—$OCH_2$—, —$CH_2CH_2O$—, —$OC_3H_6$—, and —$OC_4H_8$—); —$C(CN)_2$—; hydroxyl substituted alkyl (—(CHOH)—); and halide substituted alkyl (—$C(CCl_3)_2$—, —$C(CBr_3)_2$—, and —$C(CF_3)_2$—).

Further disclosed are compositions of matter as above made by polymerizing the resin monomers using methods including free-radical polymerization, cationic polymerization, or anionic polymerization.

In various embodiments, the compositions of matter may be dental materials that are used as restorative materials, laminate veneers, denture repairing materials, and sealants.

In other embodiments the compositions of matter are dental materials that are used as dental adhesives, resin reinforced cements, and resin bonding or ceramic restorations.

DESCRIPTION OF THE DRAWINGS

The detailed description refers to the following figures m which like numerals refer to like objects, aid in which:

FIGS. 3A-3G illustrate chemical structures/formulas of resin monomers;

FIG. 7 illustrates the resistance of the TEG-DVBE monomer to esterase degradation;

FIGS. 8A and 8B illustrate, respectively, degradation profiles for Bis-GMA and TEG-DMA monomers at different incubation time with esterases;

DETAILED DESCRIPTION

Figure 1:
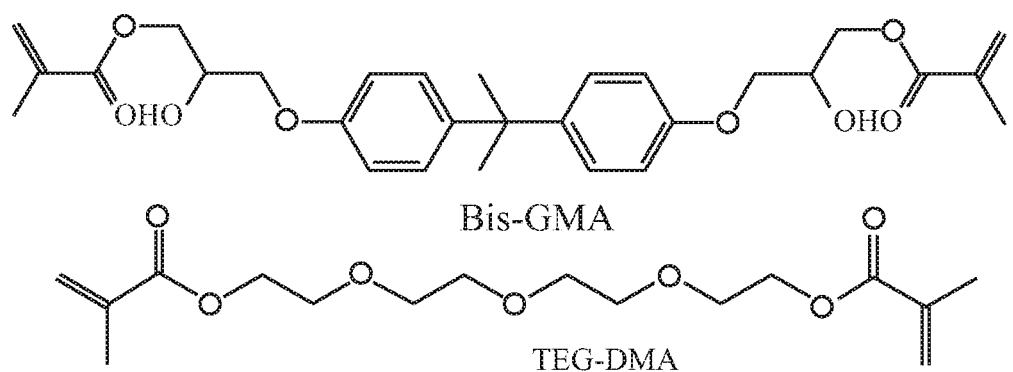
FIG. 1 illustrates bisphenol A glycidyl methacrylate/triethylene glycol dimethacrylate (Bis-GMA/TEG-DMA) compounds.

FIG. 1 illustrates current bisphenol A glycidyl methacrylate/triethylene glycol dimethacrylate (Bis-GMA/TEG-DMA) compounds that are used in a variety of applications. One such application is as a component of a dental composite restorative system for cavities. This current dental composite restorative system further includes: 1) reinforcing filler particles treated with coupling agents (containing hydrolyzable ester connecting groups) to bind the resin to the particles, and 2) dentin/enamel bonding agents (also containing hydrolyzable ester connecting groups). However, current dental composite restorative systems made of methacrylate-based resin have too short a service life with less than satisfactory durability and esthetics over time. The short service life of these systems coupled with leaching of unreacted monomers, bisphenol A (BPA), and degradation products from these systems may require frequent dental rework and may raise other health issues. Although improvements have been made in the composite polymer and filler properties (see U.S. Pat. No. 7,241,856), the polymer chemistry (methacrylate-based resins) is fundamentally unchanged since its introduction in the early 1960s (see U.S. Pat. Nos. 3,066,112; 3,179,623; and 3,194,784).

To overcome problems inherent in current dental composite restorative systems, disclosed herein are resin monomers, resins, and resin composites comprising polymers that are BPA-free, that experience low shrinkage, and that are not susceptible to enzymatic and hydrolytic degradation. Also disclosed are methods for producing the resin monomers.

In an embodiment, the herein disclosed resins replace hydrolyzable methacrylate-based resins with BPA-free and hydrolytically stable vinylbenzyl ether based resins. As an example, three co-polymerizable compounds, Erythritol divinylbenzyl ether (E-DVBE), Triethyleneglycol divinylbenzyl ether (TEG-DVBE), and Glycine, N-2-hydroxy-3-(4-vinylbenzyloxy) (NTG-VBE) (see FIG. 2 for examples of their structures) were synthesized, purified, and evaluated as substitutes for currently used Bis-GMA, TEG-DMA, and NTG-GMA (Glycine, N-2-hydroxy-3-(2-methyl-1-oxo-2-propenyl)-oxypropyl-N-(4-methylphenyl), monosodium salt) [CAS No. 133736-31-9], respectively Dental composite restorative systems prepared with the herein disclosed resins, resin composites, and accompanying adhesives will have better durability compared with currently available Bis-GMA/TEG-DMA-based systems.

Figure 2:
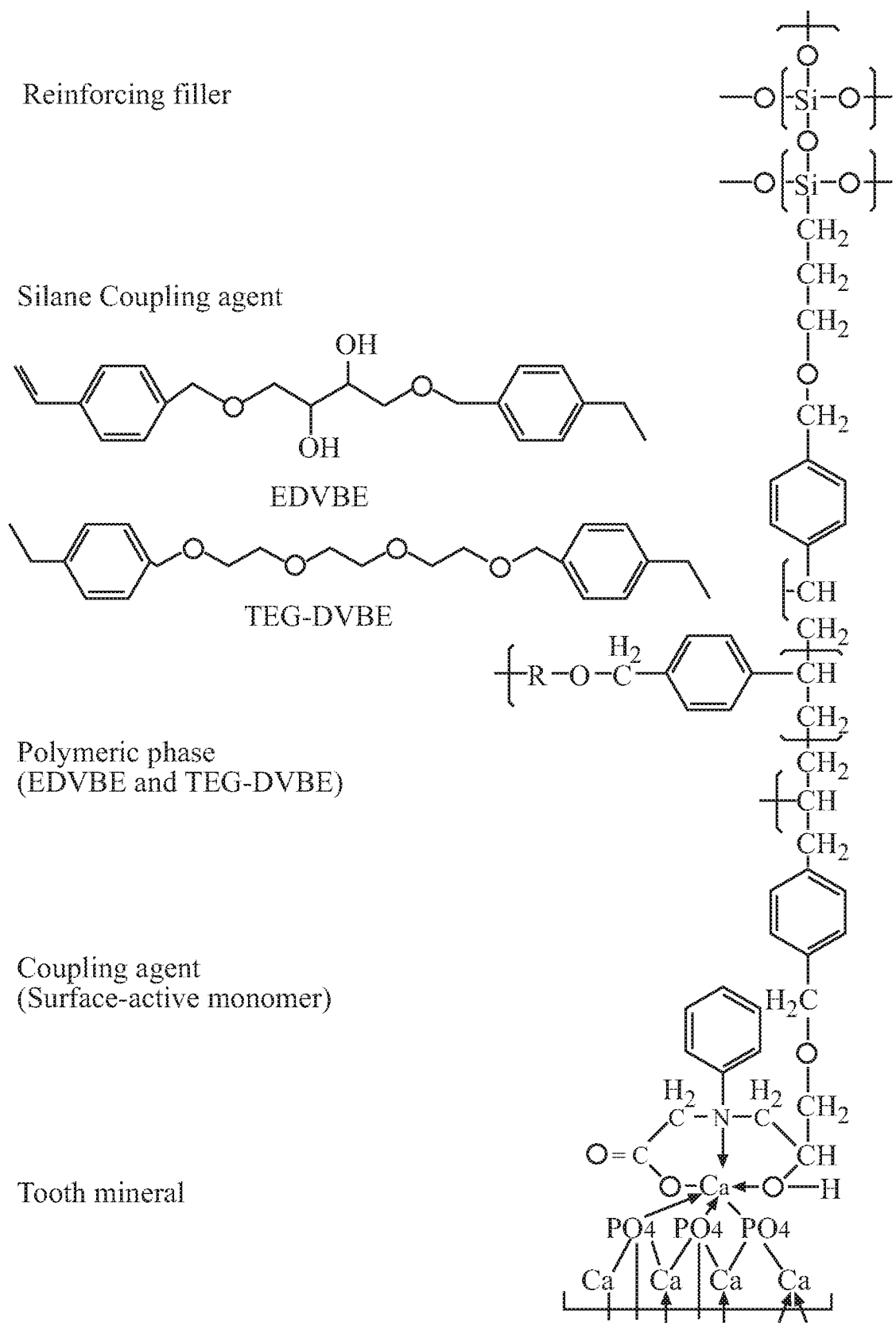
FIG. 2 illustrates an example application as a dental composite restorative system in which hydrolyzable methacrylate based-components are replaced with BPA-free and hydrolytically stable vinylbenzyl ether based components.

FIG. 2 illustrates an example application of a dental composite restorative system that uses the herein disclosed example resins and resin monomers. Dental composite restorative system 10 includes a reinforcing filler, a silane coupling agent, a polymeric phase resin network, and a surface active monomer; placed on a tooth material. The example materials illustrated in FIG. 2:

1) Include easy handling resin monomers. The E-DVBE and TEG-DVBE have two terminal double bonds, which can each readily copolymerize, and can be used in the polymeric phase resin network. The TEG-DVBE is used to adjust and control the viscosity of the monomers to obtain good handling properties of dental composite restorative systems. The NTG-VBE, incorporated in the form of the sodium, magnesium, or other salt, is the active ingredient in dentin/enamel bonding agents, can be served as a surface active monomer.

2) Eliminate all BPA moieties. Many professional publications report the dangers of BPA leaching from dental composites and sealants; these dangers could decrease patients' willingness to obtain necessary dental care.

3) Eliminate potentially hydrolysable ester groups (contained in Bis-GMA, TEG-DMA, and NTG-GMA—see FIG. 1) in either the cross-linking monomers of the composite or in its accompanying adhesive-bonding formulation. The herein disclosed materials have ether groups that are not susceptible to salivary or other esterases, and thereby are more resistant to degradation in the oral cavity.

4) Improve physical and chemical properties that can be achieved with current resins. For example, E-DVBE is an ambiphilic compound with two hydrophobic vinylbenzyl groups at its ends and a flexible hydrophilic center (two hydroxyl groups from meso-erythritol). The vicinal hydroxyl groups can more easily form clusters of hydrogen bonds with the readily accessible hydroxyl groups of other such monomers Modeling suggests that such clustering increases monomer density relative to its polymer, which should contribute to reduced polymerization shrinkage.

FIGS. 3A-3G illustrate chemical structures/formulas of the example resin monomers disclosed herein. FIGS. 3A-3G also show how different the herein disclosed resin systems are from Bis-GMA/TEG-DMA-based resin systems. Systems based on Bis-GMA/TEG-DMA contain undesirable ester groups [—C(=O)O—C—]. Many of these linking ester groups can eventually come apart by acidic, basic, or enzymatic-induced hydrolysis or saponification in a stressful intraoral environment, especially at or near polymer-tooth interfaces. Human saliva contains esterase that can hydrolyze ester-containing compounds. When subjected to thermal, mechanical and biochemical challenges, contemporary composite dental restorations can lose interfacial-sealing integrity leading to staining and secondary decay. The herein disclosed resin systems replace all of the ester groups and use only hydrolytically and enzymatically-stable ether groups.

The example resin monomers illustrated in FIGS. 3A-3G were synthesized to enable simultaneous, side-by-side, comparative testing of all restorative systems under the same environments and conditions.

FIG. 3A illustrates a general chemical structure/formula for the herein disclosed resin monomers. As can be seen, the resin monomers may include a vinylbenzyl ether group. The attached R and X groups are defined with respect to FIGS.

3B-3G. For example, for a resin monomer with one vinylbenzyl ether group, $X_1$ may be —H, —$CH_3$, or —$C_2H_5$, and —H is preferred.

FIG. 3B illustrates the chemical structure/formula of resin monomers where one vinylbenzyl ether group (n=1) is attached to multi-hydroxyl methyl group(s). These monomers are amphiphilic compounds, and they also may have diluting functions as hydroxyethylmethacrylate (HEMA). For the resin monomer of FIG. 3B: $m1$=2, 3, or 4; $X_1$ may be —H, —$CH_3$, or —$C_2H_5$; $X_2$, $X_3$, $X_6$; and/or $X_7$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_4$ and/or $X_5$ may be —H, —$CH_3$, —$OCH_3$, —$CF_3$, —F, —CL, —Br, —CN, —$C_2H_5$, —$C_3H_7$, —$C_4H_9$, —$OC_2H_5$, —$OC_3H_7$, or —$OC_4H_9$. The compound is erythritol vinylbenzyl ether (E-VBE) when all of the X groups are —H and $m_1$=2. The synthesis plan for E-VBE is shown in FIG. 4A.

FIG. 3C illustrates the chemical structure/formula of resin monomers where also one vinylbenzyl ether group (n=1) is attached to a derivative of glycine. These compounds may be an acid or the corresponding salt thereof including sodium, magnesium, calcium and strontium. For the resin monomers of FIG. 3C, $X_1$ may be —H, —$CH_3$, or —$C_2H_5$; $X_2$, $X_3$, $X_6$; and/or $X_7$ may be —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_4$ and or $X_5$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_8$ and/or $X_9$ may be —H, —OH, —$CH_3$, —$OCH_3$, —$CF_3$, —F, —Cl, —Br, —CN, —$C_2H_5$, —$C_3H_7$, or —$OC_2H_5$; $X_{10}$ and/or $X_{11}$ may be —H, —$CH_3$, —$OCH_3$, —$CF_3$, —F, —Cl, —Br, —CN, —$C_2H_5$, or —$OC_2H_5$; $X_{12}$, $X_{13}$, and/or $X_{14}$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; Y=H, Na, Ca, Mg, or Sr; and $R_1$=nothing (i.e, no functional groups), —$(CH_2)_{m2}$—, or —$(CH_2CH_2O)_{m3}$—; $m2$, $m3$=1, 2, 3, 4, or 5. More specifically, for $X_{10}$ and $X_{11}$, —H is preferred; for $X_{14}$, —$CH_3$, is preferred; for $X_{12}$ and $X_{13}$, —H is preferred; and for $X_{12}$ and $X_{13}$=—$CH_3$ and $X_{14}$=—H is highly preferred. These resin monomers are surfactants, they may replace the surfactants (e.g., NTG-GMA), in current dental restorative composite systems; e.g., as a surface active monomer in the adhesive-bonding components for dental resin composites. Compound NTG-VBE is an example when $X_1$ to $X_{13}$ are —H, $X_{14}$ is —$CH_3$, and $R_1$ is nothing. The synthesis plan for NTG-VBE is shown in FIG. 4B.

Figure 3D:
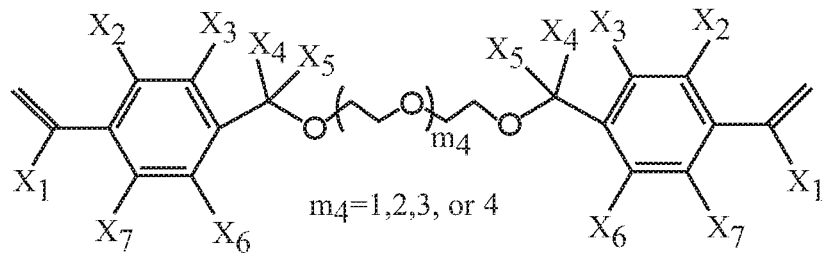
Figure 4A:
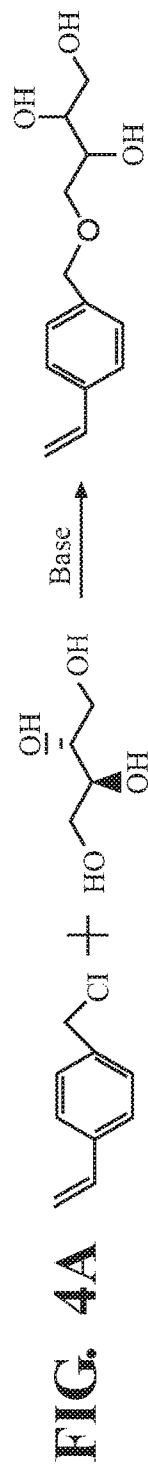
FIGS. 4A-4F outline example synthesis plans for the resin monomers shown in FIGS. 3B-3G.
Figure 4B:
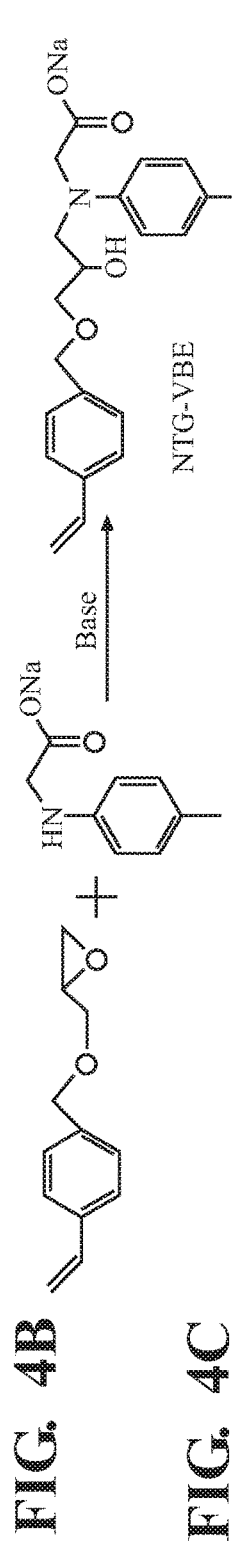
Figure 4C:
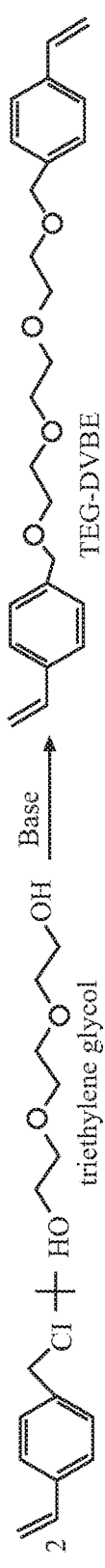

FIG. 3D illustrates the chemical structure/formula of resin monomers where two vinylbenzyl ether groups (n=2) are attached to ethoxyl group(s). For the resin monomer of FIG. 3D, $m_4$=1, 2, 3, or 4; $X_1$ may be —H, —$CH_3$, or —$C_2H_5$, $X_2$, $X_3$, $X_6$; and/or $X_7$ may be —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; and $X_4$ and/or $X_5$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$. The compound is triethyleneglycol divinylbenzyl ether (TEG-DVBE) when all of the X groups are —H and $m_4$=2. The synthesis plan for TEG-DVBE is shown in FIG. 4C.

Figure 3E:
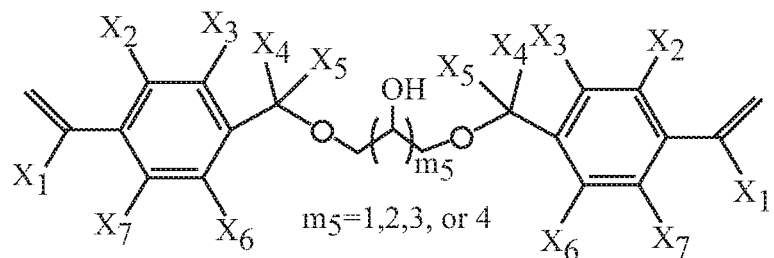
Figure 4D:
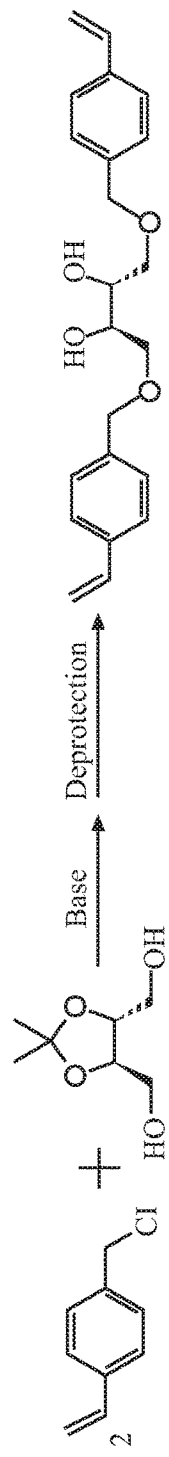
Figure 4E:
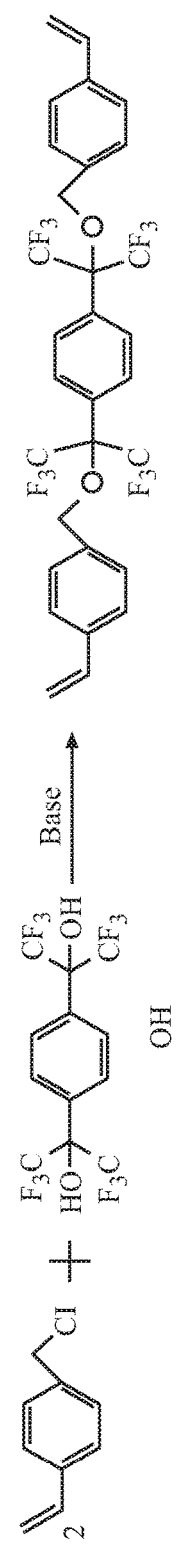

FIG. 3E illustrates the chemical structure/formula of resin monomers where two vinylbenzyl ether groups (n=2) are attached to hydroxyl methyl group(s). For the resin monomer of FIG. 3E, $m_5$=1, 2, 3, or 4; $X_1$ may be —H, —$CH_3$, or —$C_2H_5$; $X_2$, $X_3$, $X_6$; and/or $X_7$ may be —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; and $X_4$ and/or $X_5$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$. The compound is erythritol divinylbenzyl ether (E-DVBE) when all of the X groups are —H and $m_5$=2. The synthesis plan for E-DVBE is shown in FIG. 4D.

The resin monomers with two vinylbenzyl groups ether (n=2) replace the Bis-GMA/TEG-DMA based dimethacrylate resins. As an example, triethyleneglycol divinylbenzyl ether (TEG-DVBE) and erythritol divinylbenzyl ether (E-DVBE) were synthesized and purified to replace the currently-used Bis-GMA and TEG-DMA.

Figure 3F:
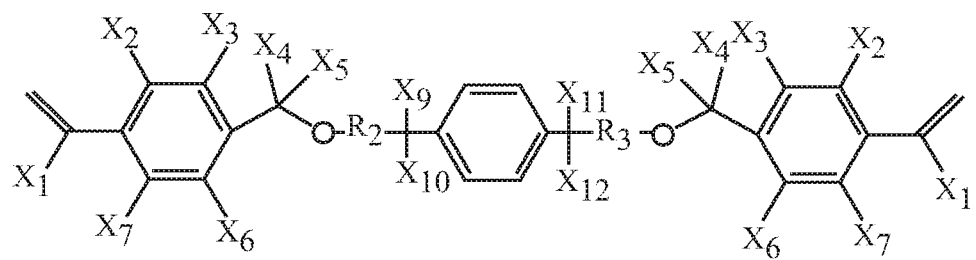

FIG. 3F illustrates the chemical structure/formula of resin monomers where two vinylbenzyl ether groups (n=2) are attached to functional groups containing a benzyl ring. These monomers have a rigid core and thus may further improve the mechanical performance of the resins. By adjusting the functional groups on $X_9$ to $X_{12}$ (for example, using —$CF_3$ instead of —$CH_3$ groups), and the chain length of $R_2$ and $R_3$, the hydrophilicity/hydrophobicity of the resin monomers may be modified to improve miscibility with other resin monomers and reduce water absorption in oral environments. For the resin monomer of FIG. 3F, $X_1$ may be —H, —$CH_3$, or —$C_2H_5$; $X_2$, $X_3$, $X_6$; and/or $X_7$ may be —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_4$ and or $X_5$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_9$, $X_{10}$, $X_{11}$, and/or $X_{12}$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$. $R_2$, and/or $R_3$ may be nothing, —$(CH_2)_{m6}$—, or —$(CH_2CH_2O)_{m7}$—; $m_6$ may be 1, 2, 3, . . . or 18; and $m7$ may be 1, 2, 3, 4, or 5. The compound is 1,4-bis(1,1,1,3,3,3-hexafluoro-2-((4-vinylbenzyl)oxy)propan-2-yl)benzene (HF-DVBE) when $X_9$, $X_{10}$, $X_{11}$ and $X_{12}$ are —$CF_3$; $R_2$ and $R_3$ are nothing; and all of the other X groups are —H. The synthesis plan for HF-DVBE is shown in FIG. 4D.

Figure 3G:
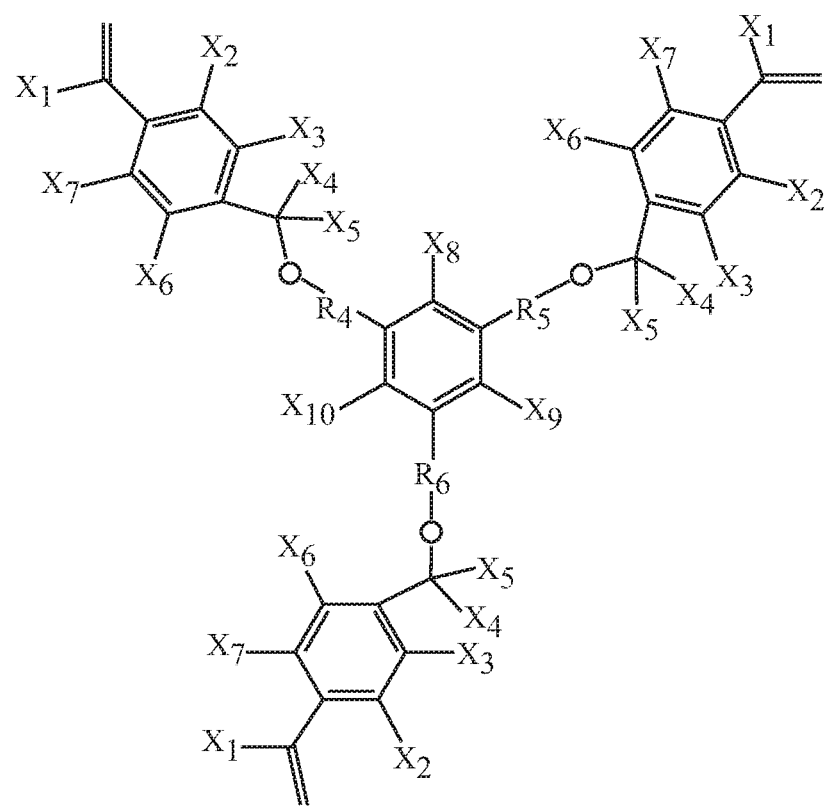
Figure 4F:
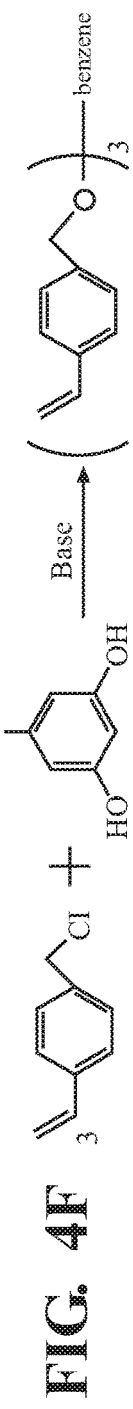

FIG. 3G illustrates the chemical structure/formula of resin monomers where three vinylbenzyl ether groups (n=3) are attached to R. These monomers have three polymerizable double bonds in each molecule and create more crosslinks using one molecule and thus change the dimension and composition of crosslinks in the resin networks. As a result, stronger, tougher and more durable resin materials may form. For the resin monomers of FIG. 3G, $X_1$ may be —H, —$CH_3$, or —$C_2H_5$; $X_2$, $X_3$, $X_6$; and/or $X_7$ may be —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_4$ and/or $X_5$ may be —H, —$CH_3$, —$OCH_3$, —$CF_3$, —F, —Cl, —Br, —CN, —$C_2H_5$, —$C_3H_7$, —$C_4H_9$, —$OC_2H_5$, —$OC_3H_7$, or —$OC_4H_9$; $X_8$, $X_9$ and/or $X10$ may be —H, —OH, —$CH_3$, —$OCH_3$, —$CF_3$, —F, —Cl, —Br, —CN, —$C_2H_5$, —$C_3H_7$, or —$OC_2H_5$; $R_4$, $R_5$, and/or $R_6$ may be nothing, —$(CH_2)_{m8}$—, or —$(CH_2CH_2O)_{m9}$—; $m_8$ may be 1, 2, 3, . . . or 18; and $m_9$ may be 1, 2, 3, 4, or 5. The compound is 4,4',4"-((((2-methylbenzene-1,3,5-triyl)tris(methylene))tris(oxy))tris(methylene))tris (vinylbenzene) (B-TVBE) when $R_4$, $R_5$, and $R_6$ are nothing; and all of the X groups are —H. The synthesis plan for B-TVBE is shown in FIG. 4F.

The subject matter of FIGS. 3A-3G define various compositions of matter that may be used, for example, in dental applications. For example, a composition may include one or more functionalized vinylbenzyl components of the formula shown in FIG. 3A covalently connected to one or more R functional components. The one or more R functional may be groups selected from a group consisting of one or more hydroxyl methyl (—CHOH—) moieties and/or derivatives thereof, one or mere ethoxy (—CH$_2$—CH$_2$—O—) moieties and/or derivatives thereof, and one or more benzene (C6H6) and/or derivatives thereof; and ether links that connect the functionalized vinylbenzyl components and the R functional components.

For these compositions of matter, the functionalized vinylbenzyloxy(s) and the R components(s) may be linked through one or more moieties chosen from a group consisting of alkyl (—CH$_2$—, —CH$_2$CH$_2$—, —C$_3$H$_6$—, —C(i-propyl)$_2$-, and —C$_4$H$_8$—); alkoxy (—OCH$_2$—, —CH$_2$CH$_2$O—, —OC$_3$H$_6$—, and —OC$_4$H$_8$—); —C(CN)$_2$—; hydroxyl substituted alkyl (—(CHOH)—); and halide substituted alkyl (—(CCl$_3$)$_2$—, —C(CBr$_3$)$_2$—, and —C(CF$_3$)$_2$—).

In FIG. 3A-3G. In an embodiment, the symbol X may refer to a hydrogen atom. In some embodiments, one or more hydrogen atoms on the vinylbenzyl components may be replaced with functional moieties (to accelerate or slow down the rate of polymerization). The functional moieties may be one or more compounds or elements chosen from a group consisting of: —CH$_3$, —C$_2$H$_5$—OCH$_3$, —CF$_3$, —F, —Cl, —Br, —CN, —C$_2$H$_5$, —C$_3$H$_7$, —C$_4$H$_9$, —OC$_2$H$_5$, —OC$_3$H$_7$, and —OC$_4$H$_9$.

In other embodiments, the R functional components may be one or multiple ethoxy (—CH$_2$—CH$_2$—O—) moieties and their derivatives. In these other embodiments, the ether links may be formed through reaction of halide(s) and alcohol(s) in the presence of a strong base, preferably sodium hydride.

In yet other embodiments, the R functional components contain hydroxyl methyl (—CHOH—) moieties and the ether links are formed through reactions of the functionalized vinylbenzyl halides and hydroxyl moieties of one of the compounds of the group consisting of glycerol, erythritol, xylitol, mannitol, and sorbitol, in the presence of a strong base, preferably sodium hydride, wherein the mole amount(s) of functionalized vinylbenzyl halides is adjusted to be within a range of the mole amount of primary hydroxyls and the mole amount of primary hydroxyls plus secondary hydroxyl moieties (—CHOH—).

In still other embodiments, the R functional components are selected from the group consisting of N-(2-hydroxypropyl)-N-(p-styryl)glycine, N-(-2-hydroxypropyl)-N-(phenyl)glycine, N-(2-hydroxypropyl)-N-(p-tolyl)glycine, N-(2-hydroxypropyl)-N-(3,5-dimethylphenyl)glycine, and N-(2-hydroxypropyl)-N-(vinylbenzyl)glycine, wherein each may be acidic, anionic, or preferably as a salt of one or more members of the group consisting of sodium, magnesium, calcium and strontium. In these embodiments, an ether link connects each of the functionalized vinylbenzyl groups with each of these R functional groups.

In some embodiments of the compositions of matter of FIGS. 3A-3G, the ether link preferably is formed from a reaction of functionalized vinylbenzyl glycidyl ether with members of the group consisting of N(H)-(p-styryl)glycine, N(H)-(phenyl)glycine, N(H)-p-tolyl)glycine, N(H)-(3,5-dimethylphenyl)glycine, and N(H)-(vinylbenzyl)glycine. Each may be anionic, or a salt of one or more members of the group consisting of sodium, magnesium, calcium and strontium. An ether link connects each of the functionalized vinylbenzyl groups with each of these R functional moieties.

In still further embodiments, a composition of matter may consist of one monomer or a mixture of monomers defined in FIGS. 3A-3G.

In the above-described compositions of matter, the resin monomer(s) may be used with cyanoacrylate based, methacrylate based, or epoxy based monomers or polymers.

FIGS. 4A-4F outline of the synthesis plans for the example resin monomers of FIGS. 3B-3G, respectively. For these plans, commercially available materials purchased from Alfa Aesar, Sigma-Aldrich and TCI America, were used as received Proton and carbon nuclear magnetic resonance ($^1$H and $^{13}$C NMR) spectra were recorded on Bruker (600 MHz) and JOEL GSX (270 MHz) spectrometers using 5 mm tubes. Chemical shifts were recorded in parts per million (ppm, δ) relative to tetramethylsilane (δ 0.00), dimethylsulfoxide-d5 (δ=2.50) or chloroform (δ=7.26). $^1$H NMR splitting patterns are designated as singlet (s), doublet (d), triplet (t), quartet (q), dd (doublet of doublets), m (multiplets), etc. All first-order splitting patterns were assigned on the basis of the appearance of the multiplet. Splitting patterns that could not be easily interpreted are designated as multiplet (m) or broad (br). Fourier transform infrared spectroscopy analysis (FTIR) was performed on a Thermo Nicolet NEXUS 670 FTIR spectrometer. Analytical thin-layer chromatography (TLC) was carried out on EMD Millipore 60 F254 pre-coated silica gel plate (0.2 mm thickness). Visualization was performed using UV irradiation (254 nm).

The detailed synthesis procedures are described with respect to the following Examples 1-5:

Example 1. Synthesis of the sodium salt of NTG-VBE. The sodium salt of N (p-tolyl) glycine (0.05256 mol) was mixed with 100 g of distilled water. The pH of the mixture was measured and adjusted to about 9 by adding a 1N aqueous NaOH solution drop-wise. The mixture turned into a clear solution. To this stirred solution, a solution containing vinylbenzyl glycidyl ether (0.05256 mol) and 0.0020 g of 2,4,6-tri-tert-butylphenol (as a stabilizer to prevent premature polymerization) in 100 mL methanol was added drop-wise. A vacuum was not used in this synthesis because the 2,4,6-tri-tert-butylphenol requires the oxygen in air to be effective. Precipitation of the sodium salt of NTG-VBE occurred on evaporation of methanol and some of the water. The sodium salt of NTG-VBE was then collected by suction filtration and recrystallized using acetone. The chemical structure was characterized by $^1$HNMR and $^{13}$CNMR. $^1$H NMR (270 MHz, DMSO-d6) δ 7.67 (d, 2H), 7.23 (d, 2H), 6.97 (d, 2H), 6.72 (d, 1H), 6.63 (d, 2H), 5.76 (d, 1H), 5.37 (s, 1H), 5.25 (s, 1H), 4.63 (s, 2H), 4.29 (s, 2H), 3.38-3.75 (m, 5H), 2.32 (s, 3H); $^{13}$C NMR (270 MHz, DMSO-d6) δ 147.6, 137.0, 136.7, 130.7, 129.9, 129.6, 128.5, 114.3, 112.8, 75.5, 73.3, 66.5, 63.3, 62.1, 21.3.

Example 2. Synthesis of 1,12-bis(4-vinylphenyl)-2,5,8,11-tetraoxadodecane. Tryethylene glycol (8.02 mL, 9.01 g, 60 mmol) in DMF (30 mL) was added dropwise to a stirred suspension of NaH (95%)(3.79 g, 150 mmol) in DMF (120 mL) at 0-4° C. under Ar$_2$ atmosphere over 30 minutes. After the reaction mixture was stirred for 2 hours at room temperature, 4-Vinylbenzyl chloride (90%)(20.3 mL, 22.0 g, 120 mmol) in DMF (50 mL) was added dropwise over 30 minutes and the reaction mixture was stirred at room temperature for 18 hours. The reaction mixture was quenched by slow addition of a saturated NH$_4$Cl aqueous solution (50 mL) at room temperature. The resulting solution was diluted with distilled water (600 mL) and extracted with ethyl acetate (3×200 mL) The combined ethyl acetate layers were washed with distilled water (2×200 mL). The organic layer was dried over anhydrous magnesium sulfate, and the solvent was removed under reduce pressure to give crude product as a dark orange oil. Flash column chromatography (silica, 30% ethyl acetate in hexane) afforded pure product as a pale yellow oil (27.5 g, 60%). The chemical structure was characterized by $^1$HNMR and $^{13}$CNMR. $^1$H NMR (600

MHz, DMSO-d$_6$) δ 7.43 (d, J=8.1 Hz, 4H), 7.29 (d, J=8.1 Hz, 4H), 6.72 (dd, J=17.8, 11.0 Hz, 2H), 5.81 (d, J=17.8, 2 H), 5.24 (d, J=11.0 Hz, 2H), 4.47 (s, 4H), 3.55 (m, 12H); $^{13}$C NMR (600 MHz, DMSO-d$_6$) δ 138.7, 136.9, 136.7, 128.2, 126.5, 114.5, 72.2, 70.4, 70.3, 69.6.

Example 3. Synthesis of 1,4-bis(1,1,1,3,3,3-hexafluoro-2-((4-vinylbenzyl)oxy)propan-2-yl)benzene. 1,4-Bis(2-hydroxyhexafluoro-isopropyl)benzene (10 g, 24.4 mmol) was added to a stirred suspension of K$_2$CO$_3$ (10.1 g, 73.2 mmol) in DMF (70 mL) under Ar$_2$ atmosphere. After reaction mixture was heated at 60° C., 4-Vinylbenzyl chloride (90%) (7.99 mL, 8.66 g, 51.2 mmol) in DMF (20 mL) was added dropwise over 30 minutes and the reaction mixture was stirred at 60° C. for 18 hours. The reaction mixture was cooled to room temperature and subsequently diluted with diethyl ether (500 mL). The resulting mixture was washed with hydrochloric acid solution (1 M, 3×250 mL), followed by washing with distilled water (2×250 mL). The organic layer was dried over anhydrous magnesium sulfate, and the solvent was removed under reduce pressure to give crude product as a yellow solid. The crude product was recrystallized in Hexanes to afford pure product as a white solid (13.5 g, 86%). The chemical structure was characterized by $^1$HNMR and $^{13}$CNMR. $^1$H NMR (270 MHz, DMSO-d6) δ 7.90 (s, 4H), 7.53 (d, J=8.2 Hz, 4H), 7.43 (d, J=8.2 Hz, 4H), 6.75 (dd, J=17.6, 10.9 Hz, 2H), 5.87 (d, J=17.6, 2 H), 5.28 (d, J=10.9 Hz, 2H), 4.64 (s, 4H); $^{13}$C NMR (270 MHz, DMSO-d6) δ 137.8, 136.5, 135.7, 130.1, 129.5, 128.7, 126.9, 115.3, 68.2.

Example 4. Synthesis of (4R,5R)-2,2-dimethyl-4,5-bis (((4-vinylbenzyl)oxy)methyl)-1,3-dioxolane. (−)-2,3-O-Isopropylidene-D-threitol (5 g, 30.8 mmol) in DMF (20 mL) was added dropwise to a stirred suspension of NaH (95%) (1.95 g, 77.1 mmol) in DMF (60 mL) at 0-4° C. under Ar$_2$ atmosphere over 30 min. After the reaction mixture was stirred for 2 hours at room temperature, 4-Vinylbenzyl chloride (90%)(9.60 mL, 10.4 g, 61.2 mmol) in DMF (50 mL) was added dropwise over 30 mm and the reaction mixture was stirred at room temperature for 18 hours. The reaction mixture was quenched by slow addition of a saturated NH$_4$Cl aqueous solution (20 mL) at room temperature. The resulting solution was diluted with distilled water (300 mL) and extracted with ethyl acetate (3×100 mL) The combined ethyl acetate layers were washed with distilled water (2×200 ml). The organic layer was dried over anhydrous potassium carbonate, and the solvent was removed under reduce pressure to give crude product as a dark orange oil.

Example 5. Synthesis of (2R,3R)-1,4-bis((4-vinylbenzyl) oxy)butane-2,3-diol. (4R,5R)-2,2-dimethyl-4,5-bis(((4-vinylbenzyl)oxy)methyl)-1,3-dioxolane crude (Example 4) was added to a stirred suspension of Dowex® 50W2X (10 g) in MeOH (200 mL) at room temperature. The reaction mixture was then stirred and refluxed at 70° C. for 18 hours. The mixture was filtered and the filtrate was evaporated under reduced pressure. The resulting mixture was diluted with distilled water and extracted with CH$_2$Cl$_2$ (3×150 mL), and the combined organic layers were washed with distilled water (3×200 mL). The organic layer was dried over anhydrous magnesium sulfate, and the solvent was removed under reduced pressure to give a crude product as a yellow solid.

These resins may be employed in composites and the corresponding adhesives with specific functions as described above. In various non-limiting embodiments, different combinations of the resin monomers may be incorporated into and polymerized to provide resin components of a denial composite restorative system such as that illustrated in FIG. 2. The resins have enzymatically and hydrolytically stable ether connections (instead of hydrolyzable ester groups) that attach the polymerizable vinylbenzyl groups of monomers of both the composite and its adhesive-bonding components.

An example instruction for the herein disclosed dental composite restorative systems calls for an etching, washing, and removal of a smear layer on tooth surfaces to be treated. The smear layer represents a structurally weak layer that contains not only disrupted and fragmented tooth structures, but also extrinsic salivary pellicle, components of biofilms and cariogenic microorganisms. It also plugs dentinal tubular openings, thereby preventing penetration of the adhesion-promoting monomeric components.

The vinylbenzyl ether groups readily homopolymerize and copolymerize with methacrylate groups and other polymerizable groups including vinyl groups. The polymerization of the vinylbenzyl compounds may be initiated using initiators that are currently used in the methacrylate systems, for example photo-initiators for wavelength 400-540 nm or dual-cure initiators for both light and chemical initiation. An example of photo-initiator is the mixture of camphorquinone (CQ) and ethyl 4-N,N-dimethylaminobenzoate (4E) at concentrations of 0.2 wt % and 0.8 wt %, respectively, of the polymer matrix. The compounds also are polymerizable using cationic and anionic polymerization mechanisms.

The herein disclosed resin composites may be used with or without fillers. The composite s reinforcing filler particles have shapes, sizes, and surface treatments that allow for a maximum filler/resin ratio by surface treatment with different coupling agents attached by covalent bonds, e.g., a combination of three types of silanes including vinylbenzyltrimethoxy silane containing polymerizable vinyl groups to provide covalent bonding and cross-linking with the monomeric phase, octyltrimethoxy silane for improved rheological properties and vinylbenzyldimethylammonium-propyltrimethoxy silane chloride, to minimize clustering or bridging and also contribute to interphase cross-linking.

The herein disclosed resins, resin monomers, and resin composites were subjected to a number of performance tests and evaluations as enumerated herein.

The degree of vinyl conversion (DC): The degree of vinyl conversion for the resins in sample disks after photopolymerization was determined using FTIR reflectance microspectroscopy (FTIR-RM). The Nicolet Continuμm FT-IR microscope (Thermo Scientific, Madison, Wis.) operated in reflectance mode and interfaced with a Nicolet 6700 FT-IR spectrophotometer was equipped with two liquid nitrogen-cooled mercury cadmium telluride detectors (MCT-A: 11,700-650 cm$^{-1}$ and MCT-B: 11,700-400 cm$^{-1}$), a video camera, and a computer-controlled x-y translation stage. Spectra were collected with 64 scans from 650 cm$^{-1}$ to 4000 cm$^{-1}$ at 8 cm$^{-1}$ spectral resolution with a beam spot size of 90 μm×90 μm. Ten spectra each of three disks (8 mm in diameter and 1 mm in thickness) of every combination of resins were obtained from the flat top and bottom of the disks. Each spot was manually focused before data collection. The reflectance spectra were proportioned against a background of a gold coated slide and transformed to absorbance spectra using the Kramers-Kronig transform algorithm for dispersion correction, which converts the reflectance spectra to absorbance-like spectra. The degree of vinyl conversion (DC) was calculated as the reduction in the vinyl peak (1634 cm$^{-1}$) height using the phenyl absorbance peak (1610 cm$^{-1}$) as an internal standard. The peak heights were determined using the ISys software (Spectral Dimensions, Olney, Md. USA). The DC was the average of 30 spectra of three disks of each sample.

Figure 5:
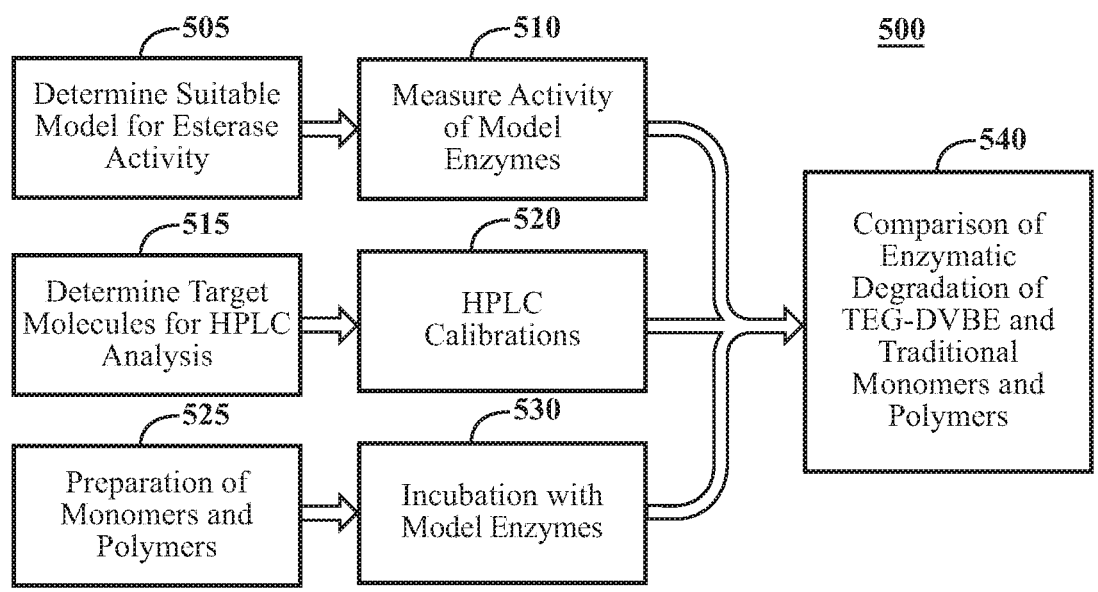
FIG. 5 illustrates and experimental process for evaluating the enzymatic degradation performance of the herein disclosed resin monomers.

Enzymatic degradation test: FIG. 5 illustrates an experimental process for evaluating the enzymatic degradation performance of the herein disclosed resin monomers. The evaluation process is based on the hypothesis that in an environment containing esterases or cariogenic bacteria, traditional Bis-GMA and TEG-DMA monomers are converted to degradation products while the herein disclosed TEG-DVBE does not degrade in the same environment. In FIG. 5, method 500 begins in block 505 by determining a suitable model for esterase activity. For example, cholesteral esterase (CE) activity may be quantified by the degradation of a substrate and as a result, the change in the optical density (OD) formed by the degradation Pseudocholinesterase activity may be tested by the degradation of butyrylthiocholin iodide (BTC) and by measuring changes in OD at a wavelength of 405 nm. According to this observation an enzyme activity may be defined that is equivalent to the optical change per minute at 405 nm, pH 7.0 and 25° C. This definition allows comparison between previous degradations studies that used a similar definition of units and substrates.

Cholesterol ester activity may be tested by the degradation of four nitrophenyl-isomers; o-nitrophenylacetate (o-NPA), p-nitrophenylacetate (p-NPA), o-nitrophenylbutyrate (o-NPB) and p-nitrophenylbutyrate (p-NPB) by measuring changes in OD at a wavelength of 410 nm and defining the CE activity as the change of absorbance of 0.01 OD per minute at 410 nm at pH 7.0 and 25° C.

In block 510, the esterase activity of model enzymes is measured and in block 515, target molecules are determined for HPLC measurement.

Figure 6:
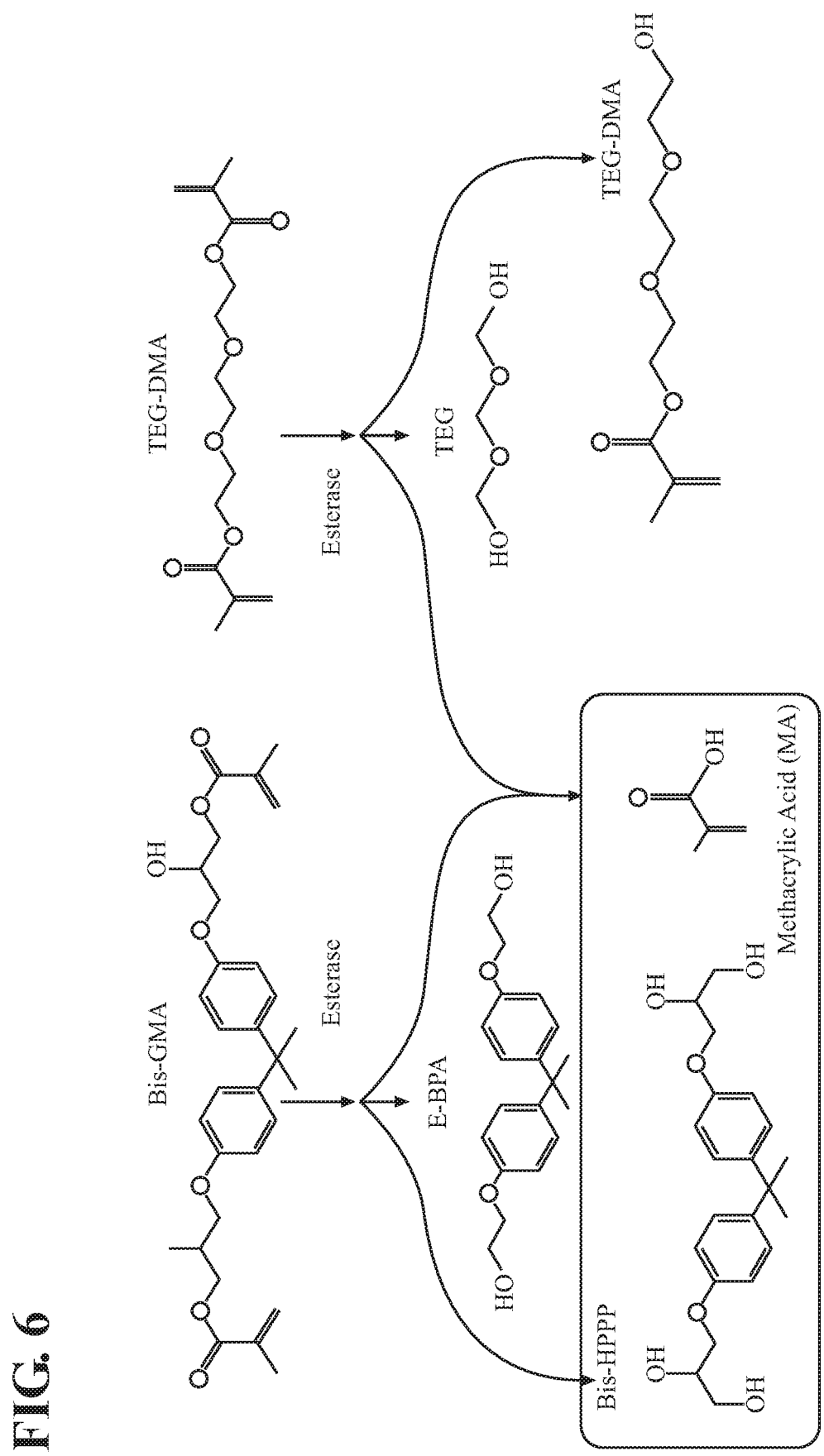
FIG. 6 illustrates degradation products produced by the interaction of current resin monomers and esterase enzymes.

Referring to FIG. 6, which illustrates degradation products produced by the interaction of current resin monomers, specifically Bis-GMA and TEG-DMA, and esterase enzymes, methacrylic acid (MA) and 2,2-Bis[4(2,3-hydroxypropoxy)phenyl]propane (bis-HPPP) are seen as possible candidates (target molecules) for the HPLC analysis. Bis-HPPP is an organic compound structurally related to bisphenol A.

Returning to FIG. 5, the method 500 continues in block 520 with HPLC calibrations. In block 525, the monomers and polymers are prepared and in block 530 the monomers and polymers are incubated with the model enzymes. Finally, in block 540, the degradation of current and the herein disclosed resins are compared.

The inventors of the herein disclosed resin monomers (TEG-DVBE) performed the method 500 to compare degradation of TEG-DVBE and traditional resin monomers (Bis-GMA and TEG-DMA) caused by the presence of esterase enzymes. The degradation compounds were detected and quantified with HPLC. After 24 hours incubation with the enzymes, no degradation was found in new resin monomers. Both Bis-GMA and TEG-DMA were decomposed dramatically by enzymes. Also evaluated was the resistance of new polymers made of TEG-DVBE and traditional polymers made of a mixture of Bis-GMA and TEG-DMA in 1:1 mass ratio to esterase enzymes. After 16 days challenge with the enzymes, no degradation was found in new polymers. The traditional polymers showed significant degradation by the enzymes. The test materials and methods are described below. Enzyme preparation began with cholesterol esterase derived from *Pseudomonas* bacteria (CE, C9281, Sigma, Saint Louis, Mo., USA) and Pseudocholinesterase from horse serum (PCE, C4290 Sigma, Saint Louis, Mo., USA), which were reconstituted at desired concentrations in phosphate-buffered saline (D-PBS, 14190-144, Gibco®, Grant Island, N.Y., USA) and sterile filtered using a 0.22 μm filter. The prepared enzyme solutions used for replenishing enzyme activity in the biodegradation experiments were stored at −20° C. until needed.

Enzyme activity assay (i.e., CE activity) was determined by para-nitrophenyl acetate (p-NPA) hydrolysis assay. P-NPA substrate (N8130, Sigma, Saint Louis, Mo., USA) was prepared by dissolving p-NPA in methanol (100 mM p-NPA), and diluting with a 100 mM sodium acetate buffer pH 5.0, to give a final p-NPA concentration of 1 mM. In a typical CE activity assay 50 μL p-NPA solution, 50 μL of CE solution (1 unit/mL) and 100 μL sodium phosphate buffer (50 mM), pH 8.8, were added to a 96-well plate to give a final pH of 7.0, and the change of absorbance over time was measured at 410 nm at 25° C. using a SpectraMax Microplate reader (Molecular Devices, Sunnyvale, Calif., USA). One unit of CE activity is defined as a change of absorbance of 0.01 per minute. CE enzyme inhibition was assessed with the addition of 4 μL of phenylmethanesulfonylfluoride (PMSF, 50 mM in anhydrous ethanol). PCE (1 unit/mL) activity was determined with acetylcholinesterase activity assay kit (MAK119, Sigma, Saint Louis, Mo., USA) by measuring a change in absorbance at 412 nm, using butylthiocholine (BTC) as a substrate. One unit of PCE activity was defined as the formation of 1.0 μmol of butyrate released per 1 mL of enzyme per minute at pH 7.5 and 25° C.

For polymer preparation, the composition of conventional resin was 50:50 wt % Bis-GMA TEG-DMA (Esstech, Essington, Pa., USA) with 0.2 wt % Camphorquinone (CQ, 124893, Aldrich, Saint Louis, Mo., USA) and 0.8 wt % ethyl 4-(dimethylamino)benzoate (DMAEMA, E24905, Aldrich, Saint Louis, Mo. USA as the photoinitiator system TEG-DVBE was mixed with 1 wt % IIRGACURE 819 (I-819) and 1 wt % bis(4-tert-butylphenyl)iodonium hexafluorophosphate (DPI) as a photoinitiation system. Photoinitiation systems for each composition were selected to achieve resins with high degree of conversion. Monomer samples were filled into a 3 mm radius 1 mm height cylindrical Teflon mold, and between two Mylar films at the top and the bottom to prevent oxygen-inhibition of the surface layer. Additionally, glass slides were used in order to flatten the surface. The samples were photocured with a Triad 2000 visible light curing unit (Dentsply Trubyte, York, Pa., USA) for 1 minute on each side. The hardened pellets with a 75 mm2 surface area were post-cured overnight in a vacuum oven at 60° C., then incubated in D-PBS at 37° C. with stirring for 24 hours to remove any unreacted monomers. Pellets were then rinsed with distilled water and vacuum dried until they reach a constant mass.

For monomer degradation, Bis-GMA, TEG-DMA, and TEG-DVBE monomers were each dissolved in DMSO (20 mM monomer), and diluted in D-PBS to give a monomer concentration of 0.4 mM. Monomer solutions (750 μL) were incubated with CE or PCE (750 μL, 2 units/mL) for 24 hours at 37° C. (n=3) PMSF at 1.0 mM and 0.5 mM were used as negative controls for CE and PCE respectively. At 1, 8, and 24 hours of incubation, 400 μL of media was removed from each sample and the enzyme activity was inhibited with the addition of 266 μL methanol. Samples were centrifuged at 16000 rcf for 30 minutes to eliminate large particles and stored at 4° C. until analysis with HPLC.

For polymer degradation, cured polymer pellets were incubated with 500 μL 1 unit/mL CE or PCE, with media volume to polymer resin surface area ratio of 6.6 ul per mm, for up to 16 days at 37° C. (n=3). PMSF at 10 mM and 0.5 mM were used as negative controls for CE and PCE, respectively. The incubation media was replaced every 48 hrs to maintain nominal enzyme activity. Each pooled media was quenched with the addition of 400 μL methanol. The media from 2, 8, and 16 days of incubation periods were pooled for HPLC analysis. Pooled were centrifuged at 16000 rcf for 30 minutes and stored at 4° C. until analysis with HPLC. Samples were also centrifuged for 30 minutes to eliminate large particles and stored at 4° C. until analysis with HPLC.

For HPLC analysis, an Agilent 1290 Infinity Binary HPLC System was used for the chromatographic separation and quantification of the degradation products. Specifically, the disappearance of TEG-DMA, Bis-GMA and TEG-DVBE monomers, as well as the appearance of methacrylic acid (MA, 155721, Aldrich, St. Louis, Mo., USA) derived from TEG-DMA and Bis-GMA and bishydroxy propoxy phenyl propane (bis-HPPP, 15137, Fluka, Saint Louis, Mo., USA) from Bis-GMA as degradation products where of interest. A Zorbex Extend 5 μm C18 4.6×250 mm column (770450-902, Agilent Technology, Santa Clara, Calif., USA) was used for the separation of products. The mobile phase consisted of 2 mM buffer solution of HPLC-grade ammonium acetate (AX1222, EMD Chemicals Inc., Billerica, Ma., USA) with pH adjusted to 3.0 with 6.0 N hydrochloric acid (A144-500, Fisher Scientific, Fair Lawn, N.J., USA) and HPL-grade methanol (MX0475, EMD Chemicals Inc., Billerica, Mass., USA). The separation was achieved with 50% to 100% methanol in ammonium acetate buffer gradient for 30 minutes in order to provide comparison with reported tests results for current monomers. Degradation products were detected by absorbance at 215 nm using a 1290 Infinity variable wavelength UV detector. Calibration curves were created by linear correlation of peak area to known concentrations of the analytes in methanol and the amount of products formed from both monomer and polymer degradation were analyzed.

FIG. 7 is a chromatogram of the TEG-DVBE monomer exposed to an environment of the enzymes CE and PCE and the solvent D-PBS, and shows absorbance of these molecules versus time. The HPLC profiles of FIG. 7 illustrate the resistance of the TEG-DVBE monomer to esterase degradation. As can be seen, no degradation products were found in any of the conditions.

Figure 8B:
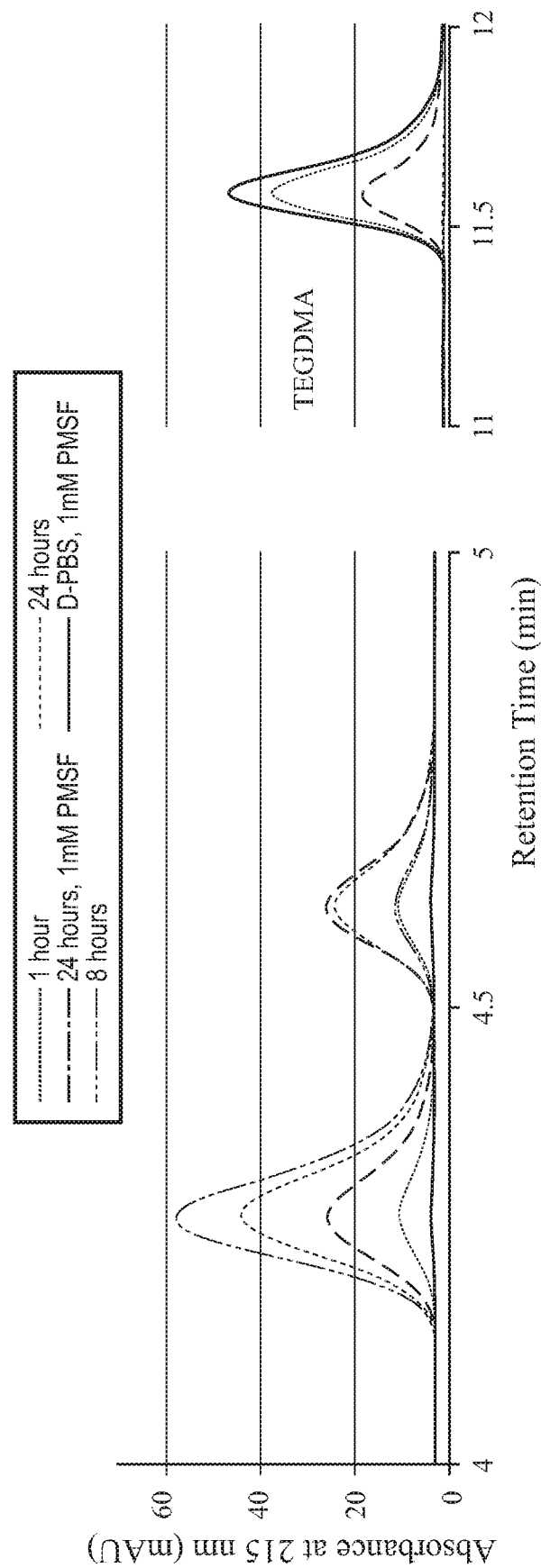

FIGS. 8A and 8B illustrate, respectively, degradation profiles for Bis-GMA and TEG-DMA monomers up to 24 hours FIG. 8A illustrates the degradation of the Bis-GMA monomer in the presence of the CE enzyme. The first plot illustrates absorbance of MA. The second plot illustrates absorbance of Bis-HPPP. The third plot illustrates absorbance of Bis-GMA.

FIG. 8B illustrates the degradation of TEG-DMA in the presence of the PCE enzyme up to 24 hours. The first plot illustrates absorbance of MA and the second plot illustrates the absorbance of TEG-DMA.

Figures 9A, 9B:
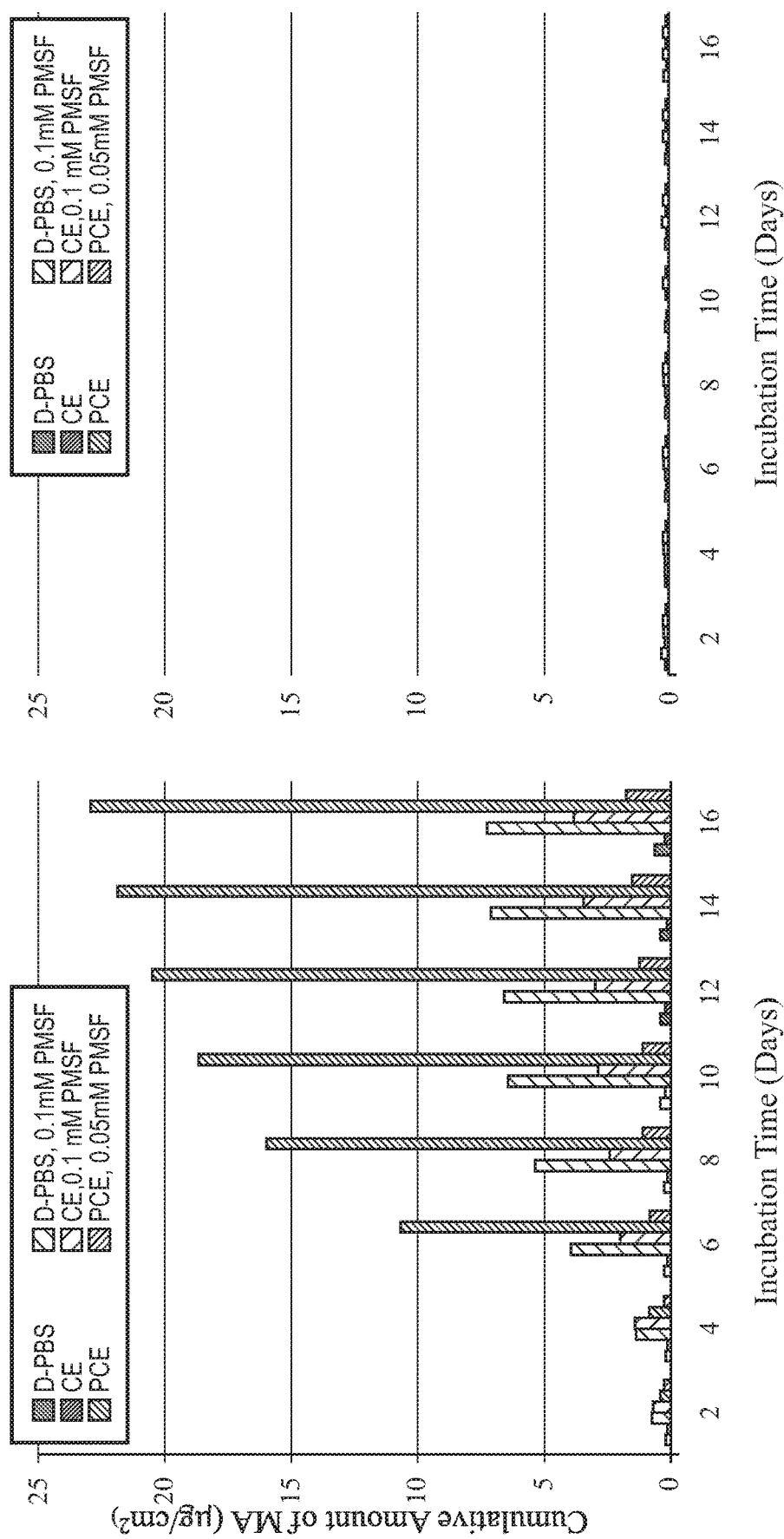
FIGS. 9A and 9B illustrate, respectively, the degradation of Bis-GMA/TEG-DMA polymers and the degradation resistance of TEG-DVBE polymers in the presence of the esterase enzyme.

FIGS. 9A and 9B illustrate, respectively, the degradation of Bis-GDMA and TEG-DMA monomers and the degradation of TEG-DVBE monomers in the presence of the esterase enzyme. Both figures plot incubation time (in days) versus cumulative absorption of MA in the presence of CE, PCE, and D-PBS. As can be seen, the Bis-GMA and TEG-DMA monomers show significant accumulation of MA while (in FIG. 9B), TEGVBE shows negligible accumulation of MA.

Figure 10A:
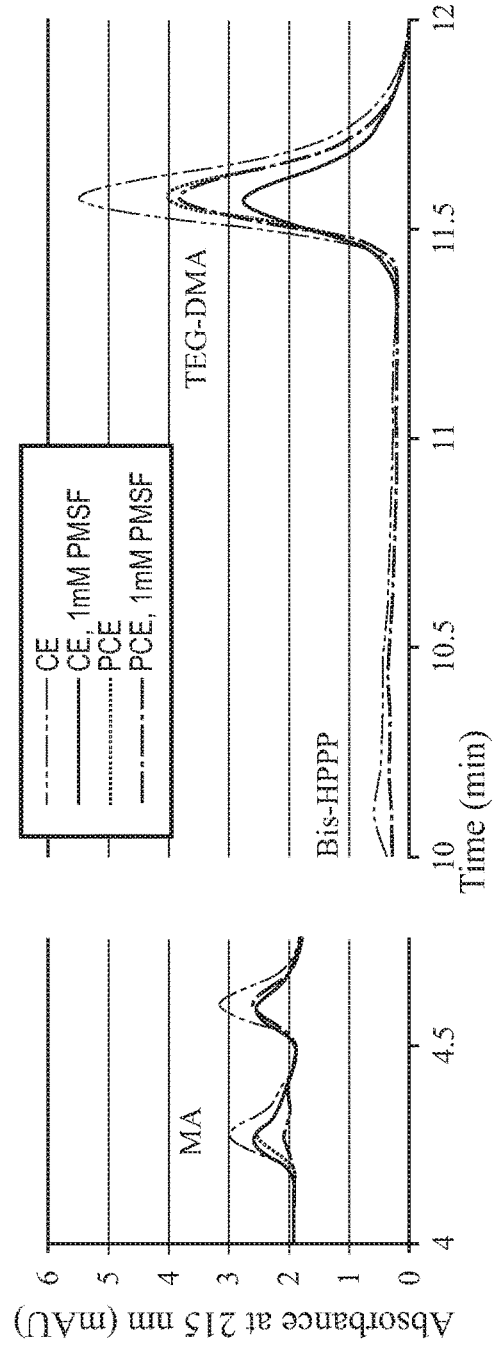
FIGS. 10A and 10B are HPLC profiles illustrating degradation of Bis-GMA/TEG-DMA polymers and the degradation resistance of TEG-DVBE polymers.
Figure 10B:
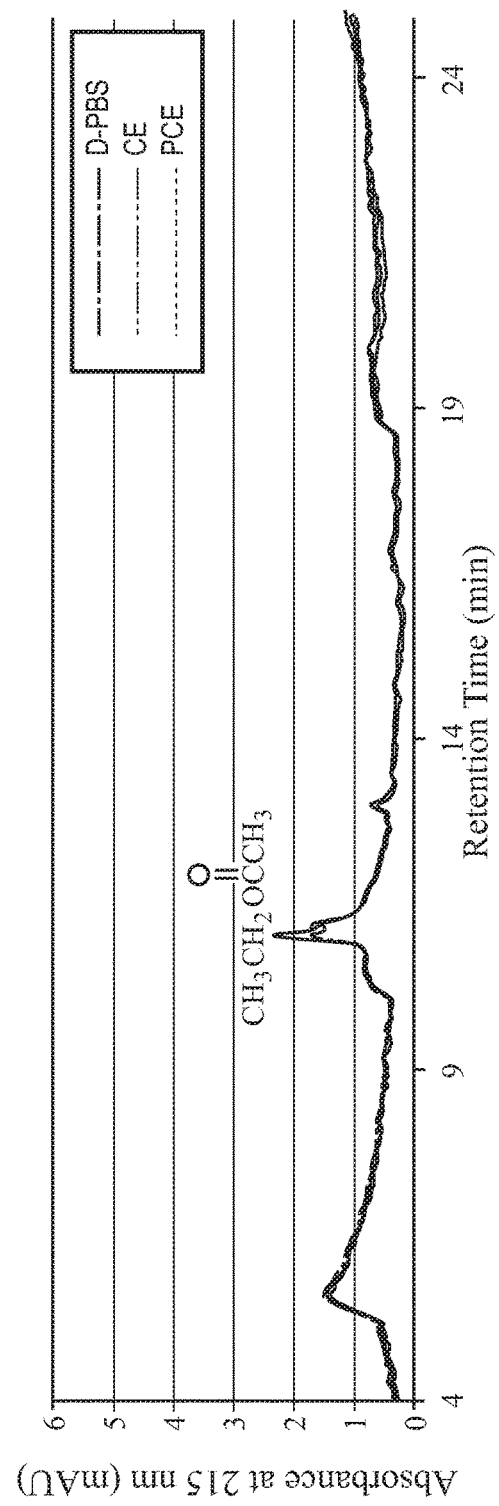

FIGS. 10A and 10B are chromatograms illustrating degradation of Bis-GDMA and TEG-DMA monomers and the TEG-DVBE monomer.

The above description refers to resins, resin composites, and adhesives for use in a dental composite restorative system. However, these materials in various combinations may be used in other systems where ester-based degradation and BPA-free conditions are a concern. For example, the materials may be used in certain food-packing applications, and in prosthetic devices.

We claim:

1. A polymerizable dental resin composition, comprising:
a reaction product of a resin monomer having one or more functionalized vinylbenzyl ether groups n of the formula

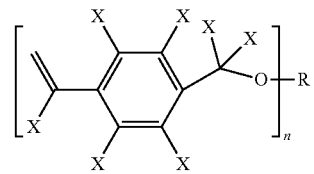

covalently bonded to one or more R functional components;
wherein n is 1 or greater than 1,
wherein the X components are one of a hydrogen atom and one or more functional moieties to control the rate of polymerization, the functional moieties being one or more compounds or elements selected from a first group consisting of —CH$_3$, —C$_2$H$_5$, —OCH$_3$, —CF$_3$, —F, —Cl, —Br, —CN, —C$_2$H$_5$, —C$_3$H$_7$, —C$_4$H$_9$, —OC$_2$H$_5$, —OC$_3$H$_7$, and —OC$_4$H$_9$,
wherein the R functional components are selected from a second group consisting of N-(2-hydroxypropyl)-N-(p-styryl)glycine, N-(2-hydroxypropyl)-N-(phenyl)glycine, N-(2-hydroxypropyl)-N-(p-tolyl)glycine (NTG-VBGE), N-(2-hydroxypropyl)-N-(3,5-dimethylphenyl)glycine, and (vinylbenzyl)glycine,
wherein each of the R functional components may be acidic, anionic, or a salt of one or more members selected from a third group consisting of sodium, magnesium, calcium, and strontium, and
wherein an ether link connects each of the functionalized vinylbenzyl groups with each of the R functional groups.

2. The polymerizable resin composition of claim 1 used as dental materials comprising restorative materials, laminate veneers, denture repairing materials, dental adhesives, resin reinforced cements, resin bonding of ceramic restorations, and sealants.

3. The polymerizable resin composition of claim 1, wherein the resin monomers are used as dental materials with or without fillers.

* * * * *